United States Patent [19]

Yoneoka

[11] 4,319,037

[45] Mar. 9, 1982

[54] PROCESS FOR PRODUCING METHYL FORMATE

[75] Inventor: Mikio Yoneoka, Niigata, Japan

[73] Assignee: Mitsubishi Gas Chemical Company, Inc., Tokyo, Japan

[21] Appl. No.: 938,344

[22] Filed: Aug. 31, 1978

Related U.S. Application Data

[63] Continuation of Ser. No. 786,408, Apr. 11, 1977, abandoned.

[30] Foreign Application Priority Data

Apr. 16, 1976 [JP] Japan .................................. 51-43294
May 7, 1976 [JP] Japan .................................. 51-51868

[51] Int. Cl.³ ........................ C07C 67/40; C07C 69/06
[52] U.S. Cl. .................................. 560/239; 252/462; 252/463; 252/476
[58] Field of Search ................. 560/239; 252/462, 463, 252/476

[56] References Cited

U.S. PATENT DOCUMENTS

| | | | |
|---|---|---|---|
| 1,400,195 | 12/1921 | Wilkie | 560/239 |
| 2,136,613 | 11/1938 | Guinot | 560/239 |
| 2,504,497 | 4/1950 | Charles et al. | 252/463 |
| 2,522,676 | 9/1950 | Harton | 560/239 |

FOREIGN PATENT DOCUMENTS

673337 1/1930 France .

OTHER PUBLICATIONS

Asakawa et al., Catalyst, vol. 4, No. 4 (1962), 375-379.

*Primary Examiner*—Vivian Garner
*Attorney, Agent, or Firm*—Browdy and Neimark

[57] ABSTRACT

A process for producing methyl formate which comprises dehydrogenating methanol in vapor phase in the presence as a catalyst of copper and at least one element selected from the group consisting of elements of Group IIIA (including the rare earths) of the periodic table, of Group IVA and of the actinides is disclosed.

13 Claims, No Drawings

PROCESS FOR PRODUCING METHYL FORMATE

This is a continuation of application Ser. No. 786,408, filed Apr. 11, 1977, now abandoned.

BACKGROUND OF THE INVENTION

This invention relates to a process for producing methyl formate which comprises dehydrogenating methanol in vapor phase.

A process for producing methyl formate which comprises dehydrogenating methanol in the presence of a certain catalyst is known. For example, copper (French Pat. No. 673,337), catalyst obtained by reducing oxides of copper, nickel, chrome and iron (U.S. Pat. No. 1,400,195) and catalyst obtained by treating copper-aluminum alloy with an aqueous alkaline solution (U.S. Pat. No. 2,504,497) were known as such catalysts. However, these patents do not disclose the yield of methyl formate obtained. I have found that when methanol is dehydrogenated in the presence of copper, methyl formate can not be obtained with excellent selectivity.

SUMMARY OF THE INVENTION

The present invention has been proposed for overcoming such shortcoming in the prior art.

Therefore, an object of this invention is to provide a process for producing methyl formate from methanol with high selectivity.

This invention relates to a process for producing methyl formate by dehydrogenating of methanol in the vapor phase in the presence as a catalyst of copper and at least one element selected from the group consisting of elements of Group IIIA (including the rare earth elements) of the periodic table, elements of Group IVA of the periodic table and actinide elements; and more specifically to said process wherein the copper component in the catalyst is the one obtained by baking basic copper carbonate.

The periodic table employed in the present invention is the one given in THE ELEMENTS OF PHYSICAL CHEMISTRY, written by Samuel Glasstone, published by D. Van Nostrand Company, Inc.

In the catalyst components employed in the present invention, the atomic ratio of copper to the elements of Group IIIA (including the rare earths), the elements of Group IVA or actinide elements may be in the range of from about 1:0.01 to about 1:2, preferably from about 1:0.05 to about 1:1.

Examples of Group IIIA include scandium, yttrium, lanthanum, cerium, praseodymium, neodymium, samarium, promethium, europium, gadolinium, terbium, dysprosium, holmium, erbium, thulium, ytterbium, and lutecium. Examples of the elements of Group IVA include titanium, zirconium and hafnium. Examples of actinides include thorium, protactinium, uranium, neptunium, plutonium and americium.

A process for producing the catalyst composed of copper and other element(s) is not critical. Conveniently, the catalyst may be prepared from compounds, such as hydroxides, oxides, carbonates, an inorganic acid salt or an organic acid salt containing copper and other element(s). The catalyst may also be prepared from a mixture of compounds containing copper and a compound containing other element(s). Preferably, the catalyst is prepared from a mixture of basic copper carbonate and a carbonate of other element(s). Water is added to the mixture of the compound containing copper and the compound containing other element(s) to form a paste, and thereafter a uniform mixture can be formed by kneading the paste. Alternatively, the catalyst can be formed by coprecipitation. The preparing operation is as follows: The mixture of the compound containing copper and the compound containing other elements is dried, and is baked at a temperature as high as about 400° C. in an atmosphere of air or nitrogen and then is reduced in a stream of $H_2$ or CO at 200° C. to activate the resulting catalyst.

The dehydrogenating of methenol is carried out by contacting the catalyst with methanol in vapor phase to produce methyl formate. The reaction conditions depend on the kind of the catalysts employed. Conveniently, the reaction temperature may be in the range from about 100° C. to about 400° C., preferably from about 150° C. to about 300° C.; and space velocity may be in the range of from about 100 $hr^{-1}$ to about 50,000 $hr^{-1}$, preferably from about 500 $hr^{-1}$ to about 30,000 $hr^{-1}$; and the reaction may be carried out at an atmospheric pressure, a superpressure or a reduced pressure. About 0.1 mol to about 2 mol of a dilution gas, such as hydrogen, carbon monoxide or nitrogen which is non active to the reaction may be present in the reaction system per 1 mol of methanol. When methyl formate is produced from methanol, selectivity to methyl formate is relative to conversion of methanol. It is preferred to maintain the conversion of methanol at less than 60% in order to keep the selectivity to methyl formate high. When the yield of methyl formate is considered, it is preferred to maintain the conversion of methanol at more than 10%.

When methyl formate is produced by dehydrogenating methanol, the catalysts employed in the present invention give superior results to copper catalyst in respect of the selectivity to methyl formate.

The present invention is further illustrated by the following Examples. However, this invention should not be limited by these examples, and the changes and modification within the spirit and scope of this invention can be effected.

Parts and percent are by weight in the following Examples, unless otherwise specified.

EXAMPLE 1

Each of 1 mol of reagent grade (GR) copper nitrate and 1.17 mol of reagent grade (GR) anhydrous sodium carbonate was dissolved in 1 l of deionized water separately, and two of the solutions were heated to 70° C. and were mixed with each other with strong stirring, and the resulting mixture was stirred while maintaining it at 70° C. for one and half hours. The resulting mixture was allowed to stand for one hour with stirring. The precipitate was suction-filtered from the mixture. The resulting cake was sufficiently washed with deionized water and was dried at 70° C. overnight.

Each of titanium oxide, zirconium carbonate, lanthanum oxide and yttrium oxide was added to 70 g of the resulting basic copper carbonate powder so that the atomic ratio of copper to titanium, zirconium, lanthanum or yttrium amounted to 1:0.1. Water was added to each mixture to form a paste. The pastes were blended and kneaded by a kneader for 30 minutes, and were allowed to stand at 70° C. overnight. The resulting dried mixtures were crushed to particles of 2 to 5 mm size. The particles were baked at 390° C. for one and half hours in air. 3 Percent of graphite was added to each mixture on the basis of the baked mixture. The mixtures were shaped to tablets having 6 mm in diameter and 5 mm high. The tablets were crushed to 1/8 size. The resulting particles containing copper compound and other element compound were charged in a pyrex glass pipe having 20 mm inner diameter, and were maintained at 200° C. for 6 hrs in a stream of hydrogen to reduce these compounds, separately.

Reactors having 20 mm inner diameter were filled with 10 ml of each of the activated catalysts and methanol vapor was charged at a space velocity of 3500 hr$^{-1}$ from one edge of the reactor. The reaction was carried out at an atmospheric pressure at each temperature as given in Table 1. The results are shown in Table 1.

TABLE 1

| Further catalyst component added to copper | Reaction temp. °C. | Conversion of methanol % | Selectivity to methyl formate % | Yield of methyl formate % |
|---|---|---|---|---|
| Titanium | 160 | 15.2 | 96.1 | 14.6 |
|  | 181 | 29.0 | 86.9 | 25.2 |
|  | 202 | 40.7 | 72.9 | 29.7 |
| Zirconium | 180 | 24.8 | 94.3 | 23.4 |
|  | 198 | 35.0 | 87.1 | 30.5 |
|  | 219 | 45.2 | 78.8 | 35.6 |
|  | 242 | 52.9 | 73.6 | 38.9 |
| Lanthanum | 169 | 18.3 | 96.1 | 17.6 |
|  | 180 | 26.0 | 94.6 | 24.6 |
|  | 194 | 30.7 | 93.1 | 28.6 |
|  | 211 | 37.4 | 89.2 | 33.4 |
|  | 226 | 43.7 | 85.1 | 37.2 |
|  | 243 | 49.5 | 79.4 | 39.3 |
| Yttrium | 179 | 23.0 | 94.2 | 21.7 |
|  | 198 | 34.0 | 88.0 | 29.9 |
|  | 219 | 43.6 | 77.6 | 33.8 |

EXAMPLE 2

The catalyst employed was the copper-lanthanum prepared in Example 1. The dehydrogenating reaction of Example 1 was repeated except that 0.13 mol of hydrogen or carbon monoxide coexisted in 1 mol of methanol, and the space velocity was 3750 hr$^{-1}$. The results are shown in Table 2.

TABLE 2

| Co-existing gas | Reaction temperature °C. | Conversion of methanol % | Selectivity to methyl formate % | Yield of methyl formate % |
|---|---|---|---|---|
| H$_2$ | 170 | 17.2 | 97.0 | 16.7 |
|  | 180 | 24.4 | 95.1 | 23.2 |
|  | 195 | 29.4 | 93.0 | 27.3 |
|  | 213 | 35.3 | 88.8 | 31.3 |
|  | 226 | 39.2 | 86.3 | 33.8 |
| CO | 173 | 19.3 | 97.0 | 18.7 |
|  | 181 | 27.8 | 94.3 | 26.2 |
|  | 195 | 32.0 | 92.8 | 29.7 |
|  | 210 | 39.5 | 89.3 | 35.2 |
|  | 225 | 46.5 | 85.5 | 39.7 |

EXAMPLE 3

The dehydrogenating reaction of Example 1 was repeated using copper-lanthanum catalyst except that the space velocity was changed as shown in Table 3. The results are shown in Table 3.

TABLE 3

| Space velocity of methanol vapor hr$^{-1}$ | Reaction temperature °C. | Conversion of methanol % | Selectivity to methyl formate % | Yield of methyl formate % |
|---|---|---|---|---|
| 500 | 139 | 5.9 | 95.5 | 5.6 |
|  | 150 | 16.5 | 92.3 | 15.2 |
|  | 164 | 21.9 | 90.0 | 19.7 |

TABLE 3-continued

| Space velocity of methanol vapor hr$^{-1}$ | Reaction temperature °C. | Conversion of methanol % | Selectivity to methyl formate % | Yield of methyl formate % |
|---|---|---|---|---|
|  | 180 | 27.7 | 85.2 | 23.6 |
|  | 200 | 28.6 | 78.8 | 22.5 |
| 1,000 | 170 | 17.5 | 96.3 | 16.8 |
|  | 182 | 26.8 | 94.0 | 25.2 |
|  | 195 | 31.4 | 94.1 | 29.5 |
|  | 214 | 36.6 | 89.9 | 32.9 |
|  | 225 | 42.6 | 86.3 | 36.8 |
|  | 245 | 48.2 | 80.5 | 38.8 |
| 3,500 | 169 | 18.3 | 96.1 | 17.6 |
|  | 180 | 26.0 | 94.6 | 24.6 |
|  | 194 | 30.8 | 93.1 | 28.6 |
|  | 211 | 37.4 | 89.2 | 33.4 |
|  | 226 | 43.7 | 85.1 | 37.2 |
|  | 243 | 49.5 | 79.4 | 39.3 |
| 7,000 | 200 | 25.4 | 95.0 | 24.1 |
|  | 215 | 30.7 | 93.1 | 28.6 |
|  | 230 | 38.1 | 88.7 | 33.8 |
|  | 245 | 43.5 | 84.7 | 36.8 |
|  | 260 | 49.7 | 78.5 | 39.0 |
| 10,000 | 218 | 25.8 | 95.3 | 24.6 |
|  | 233 | 30.1 | 93.6 | 28.2 |
|  | 249 | 38.2 | 89.7 | 34.3 |
|  | 265 | 43.8 | 85.1 | 37.3 |
|  | 280 | 48.5 | 81.5 | 39.5 |

EXAMPLE 4

The dehydrogenating reaction of Example 1 was repeated using copper-zirconium catalyst, except that the atomic ratio of copper to zirconium was changed as shown in Table 4.

TABLE 4

| Atomic ratio of copper to zirconium | Reaction temperature °C. | Conversion of methanol % | Selectivity to methyl formate % | Yield of methyl formate % |
|---|---|---|---|---|
| 1:0.01 | 162 | 21.4 | 93.9 | 20.1 |
|  | 179 | 31.8 | 81.2 | 25.8 |
| 1:0.1 | 180 | 24.8 | 94.3 | 23.4 |
|  | 198 | 35.0 | 87.1 | 30.5 |
|  | 219 | 45.2 | 78.8 | 35.6 |
|  | 242 | 52.9 | 73.6 | 38.9 |
| 1:0.5 | 196 | 22.4 | 94.7 | 21.2 |
|  | 220 | 36.7 | 93.8 | 34.4 |
|  | 241 | 41.7 | 93.4 | 38.9 |
|  | 258 | 45.4 | 93.2 | 42.3 |
|  | 275 | 48.7 | 92.1 | 44.8 |
|  | 300 | 54.2 | 87.1 | 47.3 |

COMPARATIVE EXAMPLE 1

The procedure of Example 3 was repeated except that the catalyst was Raney copper sold by Kawaken Fine Chemical Co. The results are shown in Table 5.

TABLE 5

| Space velocity of methanol vapor hr$^{-1}$ | Reaction temperature °C. | Conversion of methanol % | Selectivity to methyl formate % | Yield of methyl formate % |
|---|---|---|---|---|
| 2,170 | 224 | 23.7 | 75.8 | 17.9 |
|  | 243 | 35.9 | 64.0 | 23.0 |
| 7,700 | 242 | 17.7 | 71.0 | 12.6 |
|  | 270 | 30.3 | 50.7 | 15.3 |
|  | 291 | 41.0 | 28.9 | 11.8 |

EXAMPLE 5

Each of cerium carbonate, neodymium carbonate, samarium oxide, thorium compound (precipitate obtained by adding sodium carbonate solution to thorium nitrate solution) and uranyl nitrate was added to 70 g of the basic copper carbonate powder obtained in Example 1 so that the atomic ratio of copper to cerium, neodymium, samarium, thorium or uranium amounted to 1:0.1. Water was added to each mixture to form a paste. The pastes were blended and kneaded by a kneader for 30 minutes, and were allowed to stand at 70° C. overnight. The resulting dried mixtures were crushed to particles of 2 to 5 mm size. The particles were baked at 390° C. for one and half hours in air. 3 Percent of graphite was added to each mixture on the basis of the baked mixture. The mixture was shaped to tablets having 6 mm in diameter and 5 mm high. The pellets were crushed to ⅛ size. The resulting particles containing copper compound and other element compounds were charged in a pyrex glass pipe having 20 mm inner diameter, and were maintained at 200° C. for 6 hrs in a stream of hydrogen to reduce these compounds.

Reactors having 20 mm inner diameter were filled with 10 ml of the activated catalysts, and methanol vapor was charged at space velocity of 3500 hr$^{-1}$ from one edge of the reactor. The reaction was carried out at an atmospheric pressure at each temperature as given in Table 6. The results are shown in Table 6.

TABLE 6

| Other metal added to copper | Reaction temperature °C. | Conversion of methanol % | Selectivity to methyl formate % | Yield of methyl formate % |
|---|---|---|---|---|
| Cerium | 183 | 26.4 | 90.3 | 23.8 |
| | 201 | 33.6 | 85.2 | 28.6 |
| | 222 | 38.8 | 81.7 | 31.7 |
| | 242 | 43.4 | 74.6 | 32.4 |
| Neodymium | 189 | 30.8 | 92.9 | 28.6 |
| | 210 | 41.0 | 87.2 | 35.8 |
| | 229 | 49.6 | 80.0 | 39.6 |
| | 245 | 55.7 | 70.6 | 39.3 |
| Samarium | 184 | 31.6 | 92.5 | 29.2 |
| | 205 | 40.4 | 85.7 | 34.7 |
| | 224 | 49.0 | 80.0 | 39.2 |
| | 243 | 56.5 | 70.3 | 39.7 |
| Thorium | 147 | 11.6 | 94.2 | 10.9 |
| | 159 | 21.7 | 89.1 | 19.3 |
| | 171 | 31.6 | 74.9 | 23.7 |
| Uranium | 170 | 22.8 | 93.5 | 21.3 |
| | 188 | 31.2 | 88.5 | 27.6 |
| | 212 | 40.8 | 82.6 | 33.7 |

EXAMPLE 6

The procedure of Example 5 was repeated using copper-cerium catalyst except that 0.13 mol of hydrogen or carbon monoxide coexisted in 1 mol of methanol, and the space velocity was 3750 hr$^{-1}$. The results are shown in Table 7.

TABLE 7

| Co-existing gas | Reaction temperature °C. | Conversion of methanol % | Selectivity to methyl formate % | Yield of methyl formate % |
|---|---|---|---|---|
| H$_2$ | 180 | 24.6 | 91.6 | 22.5 |
| | 200 | 31.8 | 86.2 | 27.4 |
| | 221 | 36.4 | 83.6 | 30.5 |
| | 243 | 41.5 | 76.3 | 31.6 |
| CO | 182 | 26.8 | 91.5 | 24.5 |
| | 202 | 34.2 | 86.8 | 29.7 |
| | 220 | 40.2 | 83.7 | 33.6 |
| | 241 | 45.5 | 75.7 | 34.5 |

EXAMPLE 7

The procedure of Example 5 was repeated using copper-cerium catalyst except that the space velocity was changed as shown in Table 8.

TABLE 8

| Space velocity of methanol vapor hr$^{-1}$ | Reaction temperature °C. | Conversion of methanol % | Selectivity to methyl formate % | Yield of methyl formate % |
|---|---|---|---|---|
| 500 | 153 | 17.4 | 92.0 | 16.0 |
| | 175 | 25.5 | 88.7 | 22.6 |
| | 196 | 32.0 | 80.4 | 25.7 |
| 1,000 | 180 | 25.5 | 90.3 | 23.0 |
| | 202 | 32.6 | 85.7 | 27.9 |
| | 220 | 37.8 | 82.6 | 31.2 |
| | 243 | 41.9 | 75.7 | 32.1 |
| 3,500 | 183 | 26.4 | 90.3 | 23.8 |
| | 201 | 33.5 | 85.2 | 28.6 |
| | 222 | 38.8 | 81.7 | 31.7 |
| | 242 | 43.4 | 74.6 | 32.4 |
| 7,000 | 220 | 31.6 | 91.7 | 29.0 |
| | 241 | 36.2 | 87.6 | 31.7 |
| | 263 | 38.6 | 85.6 | 33.1 |
| | 280 | 43.8 | 80.2 | 35.2 |
| 10,000 | 240 | 32.0 | 92.5 | 29.6 |
| | 265 | 36.0 | 89.6 | 32.2 |
| | 282 | 39.6 | 86.7 | 34.3 |
| | 301 | 44.5 | 82.4 | 36.7 |

COMPARATIVE EXAMPLE 2

The procedure of Example 7 was repeated except that the catalyst was Raney copper sold by Kawaken Fine Chemical Co. The results are shown in Table 9.

TABLE 9

| Space velocity of methanol vapor hr$^{-1}$ | Reaction temperature °C. | Conversion of methanol % | Selectivity to methyl formate % | Yield of methyl formate % |
|---|---|---|---|---|
| 2,170 | 224 | 23.7 | 75.8 | 17.9 |
| | 243 | 35.9 | 64.0 | 23.0 |
| 7,700 | 242 | 17.7 | 71.0 | 12.6 |
| | 270 | 30.3 | 50.7 | 15.3 |
| | 291 | 41.0 | 28.9 | 11.8 |

What is claimed is:

1. A process for producing methyl formate comprising dehydrogenating methanol in the vapor phase in the presence of a catalyst obtained by baking in air a mixture of (i) basic copper carbonate and (ii) at least one compound containing at least one element selected from the group consisting of an element of Group IIIA (including the rare earth elements) of the periodic table, an element of Group IVA of the periodic table and an actinide element, the atomic ratio of copper to said other element in said catalyst being from about 1.0:0.01 to about 1:2, followed by heating in a reducing atmosphere comprising hydrogen or carbon monoxide at a temperature sufficient to reduce and thereby to activate the catalyst.

2. The process as defined in claim 1 wherein the dehydrogenation is carried out in the presence of an inert gas.

3. The process as defined in claim 1 wherein the dehydrogenation is carried out at a space velocity of from about 100 hr$^{-1}$ to about 50,000 hr$^{-1}$.

4. The process as defined in claim 1 wherein the dehydrogenation is carried out at a temperature of from about 100° C. to about 400° C.

5. The process of claim 1 wherein the catalyst consists essentially of said copper and titanium.

6. The process of claim 1 wherein the catalyst consists essentially of said copper and zirconium.

7. The process of claim 1 wherein the catalyst consists essentially of said copper and lanthanum.

8. The process of claim 1 wherein the catalyst consists essentially of said copper and yttrium.

9. The process of claim 1 wherein the catalyst consists essentially of said copper and cerium.

10. The process of claim 1 wherein the catalyst consists essentially of said copper and neodymium.

11. The process of claim 1 wherein the catalyst consists essentially of said copper and samarium.

12. The process of claim 1 wherein the catalyst consists essentially of said copper and thorium.

13. The process of claim 1 wherein the catalyst consists essentially of said copper and uranium.

* * * * *